(12) United States Patent
Woloszko et al.

(10) Patent No.: US 11,504,182 B2
(45) Date of Patent: Nov. 22, 2022

(54) PLASMA SURGERY DEVICE

(71) Applicant: Smith & Nephew, Inc., Memphis, TN (US)

(72) Inventors: Jean Woloszko, Austin, TX (US); Johnson E. Goode, Austin, TX (US); Brent R. Dinger, Austin, TX (US)

(73) Assignee: Smith & Nephew, Inc., Memphis, TN (US)

( * ) Notice: Subject to any disclaimer, the term of this patent is extended or adjusted under 35 U.S.C. 154(b) by 450 days.

(21) Appl. No.: 16/603,501

(22) PCT Filed: Apr. 10, 2018

(86) PCT No.: PCT/US2018/026867
§ 371 (c)(1),
(2) Date: Oct. 7, 2019

(87) PCT Pub. No.: WO2018/191253
PCT Pub. Date: Oct. 18, 2018

(65) Prior Publication Data
US 2021/0282844 A1 Sep. 16, 2021

Related U.S. Application Data

(60) Provisional application No. 62/483,802, filed on Apr. 10, 2017.

(51) Int. Cl.
*A61B 18/14* (2006.01)
*A61B 18/16* (2006.01)
(Continued)

(52) U.S. Cl.
CPC .......... *A61B 18/1482* (2013.01); *A61B 18/16* (2013.01); *A61B 18/042* (2013.01);
(Continued)

(58) Field of Classification Search
CPC ........... A61B 2017/00973; A61B 2018/00309; A61B 2018/00577; A61B 2018/122;
(Continued)

(56) References Cited

U.S. PATENT DOCUMENTS 5,904,681 A * 5/1999 West, Jr. .............. A61B 18/148
606/41
7,481,807 B2 1/2009 Knudsen
(Continued)

FOREIGN PATENT DOCUMENTS

GB 2451623 2/2009
WO 2017034863 3/2017

OTHER PUBLICATIONS

Search Report for PCT/US2018/026867 dated Jun. 7, 2018, 3 pages.
(Continued)

*Primary Examiner* — Khadijeh A Vahdat
(74) *Attorney, Agent, or Firm* — Norman F. Hainer, Jr.

(57) ABSTRACT

An electrosurgical wand is provided and includes a handle and an elongate shaft coupled to the handle and extending distally from the handle along an axis. An active electrode is disposed at a distal end of the electrosurgical wand. A return electrode abuts the elongate shaft and extends along and annularly about the axis. The return electrode has a top side adjacent the active electrode and an opposite bottom side and defines a notch. A support member is disposed in the notch between the electrodes and transitions curvilinearly from the notch to define a front surface extending laterally across and axially from the return electrode. The front surface tapers downwardly from the active electrode to define a first portion defining a first convex outer surface and also extends toward the bottom side of the return electrode to define a second portion defining a second convex outer surface.

19 Claims, 8 Drawing Sheets

(51) Int. Cl.
*A61B 18/04* (2006.01)
*A61B 17/00* (2006.01)

(52) U.S. Cl.
CPC .............. *A61B 2017/00973* (2013.01); *A61B 2218/007* (2013.01)

(58) Field of Classification Search
CPC .... A61B 2018/1405; A61B 2018/1495; A61B 2018/162; A61B 2218/007
See application file for complete search history.

(56) References Cited

U.S. PATENT DOCUMENTS

| | | |
|---|---|---|
| 8,425,506 B2 | 4/2013 | Gallo |
| 8,840,610 B2 | 9/2014 | Humble |
| 8,845,576 B2 | 9/2014 | Kramer |
| D732,164 S | 6/2015 | Woloszko |
| 2005/0277915 A1 | 12/2005 | DeCesare |
| 2007/0149965 A1 | 6/2007 | Gallo |
| 2010/0204690 A1* | 8/2010 | Bigley ................. A61B 18/148 606/41 |
| 2011/0245826 A1 | 10/2011 | Woloszko |
| 2012/0179157 A1 | 7/2012 | Frazier |
| 2014/0257269 A1 | 9/2014 | Woloszko |
| 2014/0257277 A1 | 9/2014 | Woloszko |
| 2015/0245862 A1 | 9/2015 | Goode |
| 2018/0280074 A1 | 10/2018 | Goode |

OTHER PUBLICATIONS

Japanese Application Na. 2020-504296 Notice of Reasons for Rejection dated Dec. 2, 2021.
Chinese Application No. 201880023675.4 The First Office Action & Search Report dated Jun. 28, 2022.

* cited by examiner

PLASMA SURGERY DEVICE

CROSS-REFERENCE TO RELATED APPLICATIONS

This application is the U.S. national phase entry under 35 U.S.C. § 371 of International Application No. PCT/US2018/026867, filed Apr. 10, 2018, entitled "Plasma Surgery Device," which claims priority to and benefit of U.S. Provisional Application Ser. No. 62/483,802 filed Apr. 10, 2017 titled "Plasma Surgery Device", the contents of which are incorporated herein by reference in their entirety for all purposes.

BACKGROUND

Electrosurgical systems are used during surgical procedures to remove several different tissue types. For example, procedures involving the knee or shoulder may remove portions of cartilage, meniscus, and free floating and/or trapped tissue. In some cases, the removal may be a very slight removal, such as tissue sculpting, and in other cases more aggressive removal of tissue is used. Electrosurgical systems may also operate in a coagulation mode, to seal arterial vessels exposed during tissue removal, and sealing to reduce bleeding.

SUMMARY

There is provided an electrosurgical wand including a handle on a proximal end of the electrosurgical wand. An elongate shaft is coupled to the handle and extends distally from the handle along a longitudinal central axis. An active electrode is disposed at a distal end of the electrosurgical wand and has an outer face and defining an exterior periphery extending thereabout. The active electrode resides within and defines a plane spaced from and extending along and laterally from the longitudinal central axis. A return electrode abuts the elongate shaft and extends along and annularly about the longitudinal central axis. The return electrode has a top side adjacent the active electrode and a bottom side disposed remotely from the active electrode and opposite the top side. At least a portion of the return electrode is disposed proximally to the active electrode. The top side of the return electrode has a first length measured axially from the elongate shaft and the bottom side has a second length measured axially from the elongate shaft being greater than the first length to define a notch enabling the bottom side of the return electrode and the active electrode to overlap along the longitudinal central axis in an overlap region. A support member that is electrically insulative is disposed in the notch between the active electrode and the return electrode and extending axially from the return electrode. The support member is coupled to and supports the active electrode. The support member transitions curvilinearly from the notch of the return electrode axially and tapers to a distal tip adjacent the active electrode to define a front surface extending laterally across and axially from the return electrode. The front surface tapers downwardly from the active electrode to define a first portion disposed adjacent the active electrode and defining a first convex outer surface. The front surface also extends toward the bottom side of the return electrode to define a second portion disposed adjacent the bottom side of the return electrode and defining a second convex outer surface. The support member holds the active electrode a first distance from the longitudinal central axis that is greater than a second distance from the longitudinal central axis to the top side of the return electrode.

In some embodiments, the support member has a midsection disposed between the first portion and the second portion of the front surface and defining a concave outer surface axially undercutting the active electrode toward the proximal end of the electrosurgical wand.

In some embodiments, the concave section has a member radius of curvature having a center disposed on a side of the longitudinal central axis being the same as the active electrode.

In some embodiments, the notch defines a circuitous edge extending arcuately across the top side of the return electrode between a pair of corners to define an upper segment and from the pair of corners axially toward the distal end to define a pair of horizontal segments laterally opposite one another and each extending axially to end at respective shoulders and from the shoulders extending arcuately around the bottom side of the return electrode to define a lower segment and wherein the support member includes a rear edge extending along and corresponding with the circuitous edge of the return electrode.

In some embodiments, the lower segment of the circuitous edge is angled axially away from the distal end as the circuitous edge extends away from the longitudinal central axis at a lower edge segment angle relative to the longitudinal central axis.

In some embodiments, at least one of the shoulders and the corners is rounded.

In some embodiments, the electrosurgical wand further includes an aspiration channel defined within the elongate shaft and the active electrode further comprises at least one aperture that defines a suction lumen, the at least one aperture is disposed over an opening into the aspiration channel.

In some embodiments, the support member includes at least one shelf extending axially along and disposed below the exterior periphery of the active electrode and extending laterally outwardly from the support member.

In some embodiments, the at least one shelf is angled at a shelf angle relative to the outer face of the active electrode.

In some embodiments, the shelf angle is between 30 and 60 degrees.

There is also provided an electrosurgical wand comprising including a handle on a proximal end of the electrosurgical wand. An elongate shaft is coupled to the handle and extends distally from the handle along a longitudinal central axis. An active electrode is disposed at a distal end of the electrosurgical wand and has an outer face and resides within and defining a plane spaced from and extending along and laterally from the longitudinal central axis. A return electrode abuts the elongate shaft and extends along and annularly about the longitudinal central axis. The return electrode has a top side adjacent the active electrode and a bottom side disposed remotely from the active electrode and opposite the top side. At least a portion of the return electrode is disposed proximally to the active electrode. A support member that is electrically insulative is disposed between the active electrode and the return electrode and extends axially from the return electrode and is coupled to and supports the active electrode. The active electrode has an oblong shape viewed perpendicular to the plane within which the active electrode resides with a wider portion and a narrower portion narrowing with increasing distal distance from the wider portion. The active electrode is disposed distally with respect to the wider portion and defines an exterior periphery extending thereabout including a pair of side edges. The active electrode includes a plurality of protrusions extending away from the outer face of the active electrode in a direction away from the longitudinal central axis.

In some embodiments, the plurality of protrusions includes a pair of rear protrusions spaced from and on opposite sides of the longitudinal central axis in the wider portion and a pair of front protrusions spaced from and on opposite sides of the longitudinal central axis and axially spaced from the rear protrusions in the narrower portion.

In some embodiments, the pair of front protrusions each angles laterally inwardly toward the longitudinal central axis as they extend axially away from the wider portion.

In some embodiments, the pair of side edges each is slightly convex and converges with one another at an active electrode apex in the narrowing portion and connected at a truncated end being linear and extending laterally from the longitudinal central axis in the wider portion.

In some embodiments, the pair of side edges each has an edge radius of curvature having a center on an opposite side of the longitudinal central axis from the respective one of the pair of side edges.

In some embodiments, the longitudinal central axis does not intersect the plane within the periphery of the active electrode.

In some embodiments, the longitudinal central axis is parallel to the plane.

In some embodiments, the electrosurgical wand further includes an aspiration channel defined within the elongate shaft and the active electrode further comprises at least one aperture that defines a suction lumen, the at least one aperture is disposed over an opening into the aspiration channel.

Further features and advantages of at least some of the embodiments of the present invention, as well as the structure and operation of various embodiments of the present invention, are described in detail below with reference to the accompanying drawings.

BRIEF DESCRIPTION OF THE DRAWINGS

For a detailed description of example embodiments, reference will now be made to the accompanying drawings in which.

DEFINITIONS

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

Reference to a singular item includes the possibility that there are plural of the same items present. More specifically, as used herein and in the appended claims, the singular forms "a," "an," "said" and "the" include plural references unless the context clearly dictates otherwise. It is further noted that the claims may be drafted to exclude any optional element. As such, this statement serves as antecedent basis for use of such exclusive terminology as "solely," "only" and the like in connection with the recitation of claim elements, or use of a "negative" limitation. Lastly, it is to be appreciated that unless defined otherwise, all technical and scientific terms used herein have the same meaning as commonly understood by one of ordinary skill in the art to which this invention belongs.

"Ablation" shall mean removal of tissue based on tissue interaction with plasma.

"Plasma" shall mean a low temperature gas formed of vapor bubbles or a vapor layer that is capable of emitting an ionized discharge.

"Active electrode" shall mean an electrode of an electrosurgical wand which produces an electrically-induced tissue-altering effect when brought into contact with, or close proximity to, a tissue targeted for treatment.

"Return electrode" shall mean an electrode of an electrosurgical wand which serves to provide a current flow path for electrical charges with respect to an active electrode, and/or an electrode of an electrical surgical wand which does not itself produce an electrically-induced tissue-altering effect on tissue targeted for treatment.

"Top side" shall mean a first side of a return electrode of an electrosurgical wand that is on the same side of a longitudinal central axis, along which the electrosurgical wand extends, as the active electrode.

"Bottom side" shall mean a second side of a return electrode of an electrosurgical wand that is on the opposite side of a longitudinal central axis, along which the electrosurgical wand extends, as the active electrode.

Where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

DETAILED DESCRIPTION

Before the various embodiments are described in detail, it is to be understood that the disclosure is not limited to particular variations set forth herein as various changes or modifications may be made, and equivalents may be substituted, without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Figure 1:
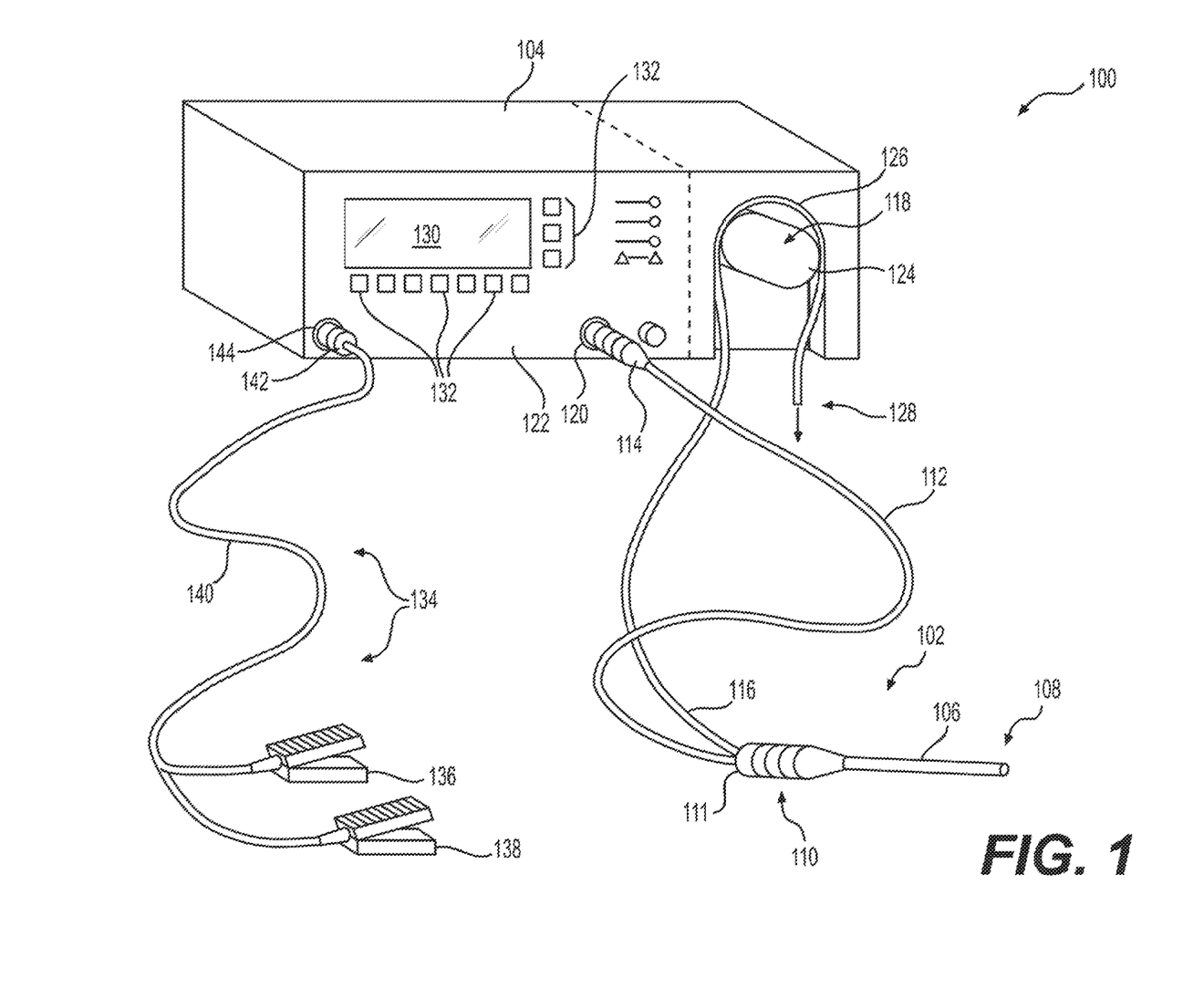
FIG. 1 shows an electrosurgical system in accordance with at least some embodiments.

FIG. 1 shows an electrosurgical system 100 in accordance with at least some embodiments. In particular, the electrosurgical system 100 comprises an electrosurgical wand 102 (hereinafter "wand 102") coupled to an electrosurgical controller 104 (hereinafter "controller 104"). The wand 102 comprises an elongate shaft 106 that defines distal end 108. The elongate shaft 106 further defines a handle 110 at a proximal end 111, where a physician grips the wand 102 during surgical procedures. The wand 102 further comprises a flexible multi-conductor cable 112 housing one or more electrical leads (not specifically shown in FIG. 1), and the flexible multi-conductor cable 112 terminates in a wand connector 114. As shown in FIG. 1, the wand 102 couples to the controller 104, such as by a controller connector 120 on an outer surface of the enclosure 122 (in the illustrative case of FIG. 1, the front surface).

Though not visible in the view of FIG. 1, in some embodiments the wand 102 has one or more internal fluid conduits coupled to externally accessible tubular members. As illustrated, the wand 102 has a flexible tubular member 116, used to provide aspiration at the distal end 108 of the wand. In accordance with various embodiments, the tubular member 116 couples to a peristaltic pump 118, which peristaltic pump 118 is illustratively shown as an integral component with the controller 104 (i.e., residing at least partially within the enclosure 122 of the controller 104). In other embodiments, an enclosure for the peristaltic pump 118 may be separate from the enclosure 122 for the controller 104 (as shown by dashed lines in FIG. 1), but in any event the peristaltic pump is operatively coupled to the controller 104. In yet still further embodiments, suction for aspiration may be provided from any suitable source, such as suction outlets available in hospital settings. The example peristaltic pump 118 comprises a rotor portion 124 (hereafter just "rotor 124") as well as a stator portion 126 (hereafter just "stator 126"). The example flexible tubular member 116 couples within the peristaltic pump 118 between the rotor 124 and the stator 126, and movement of the rotor 124 against the flexible tubular member 116 causes fluid movement toward the discharge 128.

Still referring to FIG. 1, a display device or interface device 130 is visible through the enclosure 122 of the controller 104, and in some embodiments a user may select operational characteristics of the controller 104 by way of the interface device 130 and related buttons 132. For example, using one or more of the buttons 132 the surgeon may select among energy ranges for use with the wand 102 during electrosurgical procedures.

In some embodiments the electrosurgical system 100 also comprises a foot pedal assembly 134. The foot pedal assembly 134 may comprise one or more pedal devices 136 and 138, a flexible multi-conductor cable 140 and a pedal connector 142. While only two pedal devices 136 and 138 are shown, one or more pedal devices may be implemented. The enclosure 122 of the controller 104 may comprise a corresponding connector 144 that couples to the pedal connector 142. A physician may use the foot pedal assembly 134 to control various aspects of the controller 104, such as the mode of ablation. For example, pedal device 136 may be used for on-off control of the application of radio frequency (RF) energy to the wand 102. Further, pedal device 138 may be used to control and/or set the mode of operation of the electrosurgical system. For example, actuation of pedal device 138 may switch between ablation mode and coagulation mode.

The electrosurgical system 100 of the various embodiments implements ablation which employs Coblation® technology. In particular, the assignee of the present disclosure is the owner of Coblation® technology. Coblation® technology involves the application of a radio frequency (RF) signal between one or more active electrodes and one or more return electrodes of the wand 102 to develop high electric field intensities in the vicinity of the target tissue. The electric field intensities may be sufficient to vaporize an electrically conductive fluid over at least a portion of the one or more active electrodes in the region between the one or more active electrodes and the target tissue. The electrically conductive fluid may be inherently present in the body, such as blood, or in some cases extracellular or intracellular fluid. In other embodiments, the electrically conductive fluid may be a liquid or gas, such as isotonic saline. In some embodiments, such as surgical procedures involving a knee or shoulder, the electrically conductive fluid is delivered in the vicinity of the active electrode and/or to the target site by a delivery system separate and apart from the system 100.

When the electrically conductive fluid is heated to the point that the atoms of the fluid vaporize faster than the atoms recondense, a gas is formed. When sufficient energy is applied to the gas, the atoms collide with each other causing a release of electrons in the process, and an ionized gas or plasma is formed (the so-called "fourth state of matter"). Stated otherwise, plasmas may be formed by heating a gas and ionizing the gas by driving an electric current through the gas, or by directing electromagnetic waves into the gas. The methods of plasma formation give energy to free electrons in the plasma directly, electron-atom collisions liberate more electrons, and the process cascades until the desired degree of ionization is achieved. A more complete description of plasma can be found in Plasma Physics, by R. J. Goldston and P. H. Rutherford of the Plasma Physics Laboratory of Princeton University (1995), the complete disclosure of which is incorporated herein by reference.

As the density of the plasma becomes sufficiently low (i.e., less than approximately 1020 atoms/cm$^3$ for aqueous solutions), the electron mean free path increases such that subsequently injected electrons cause impact ionization within the plasma. When the ionic particles in the plasma layer have sufficient energy (e.g., 3.5 electron-Volt (eV) to 5 eV), collisions of the ionic particles with molecules that make up the target tissue break molecular bonds of the target tissue, dissociating molecules into free radicals which then combine into gaseous or liquid species. By means of the molecular dissociation (as opposed to thermal evaporation or carbonization), the target tissue is volumetrically removed through molecular dissociation of larger organic molecules into smaller molecules and/or atoms, such as hydrogen, oxygen, oxides of carbon, hydrocarbons and nitrogen compounds. The molecular dissociation completely removes the tissue structure, as opposed to dehydrating the tissue material by the removal of liquid within the cells of the tissue and extracellular fluids, as occurs in related art electrosurgical desiccation and vaporization. A more detailed description of the molecular dissociation can be found in commonly assigned U.S. Pat. No. 5,697,882 the complete disclosure of which is incorporated herein by reference.

The energy density produced by electrosurgical system 100 at the distal end 108 of the wand 102 may be varied by adjusting a variety of factors, such as: the number of active electrodes; electrode size and spacing; electrode surface area; asperities and/or sharp edges on the electrode surfaces; electrode materials; applied voltage; current limiting of one or more electrodes (e.g., by placing an inductor in series with an electrode); electrical conductivity of the fluid in contact with the electrodes; density of the conductive fluid; and other factors. Accordingly, these factors can be manipulated to control the energy level of the excited electrons. Since different tissue structures have different molecular bonds, the electrosurgical system 100 may be configured to produce energy sufficient to break the molecular bonds of certain tissue but insufficient to break the molecular bonds of other tissue. For example, fatty tissue (e.g., adipose) has double bonds that require an energy level higher than 4 eV to 5 eV (i.e., on the order of about 8 eV) to break. Accordingly, the Coblation® technology in some modes of operation does not ablate such fatty tissue; however, the Coblation® technology at the lower energy levels may be used to effectively ablate cells to release the inner fat content in a liquid form. Other modes of operation may have increased energy such that the double bonds can also be broken in a similar fashion as the single bonds (e.g., increasing voltage or changing the electrode configuration to increase the current density at the electrodes). A more complete description of the various phenomena can be found in commonly assigned U.S. Pat. Nos. 6,355,032, 6,149,120 and 6,296,136, the complete disclosures of which are incorporated herein by reference.

Figure 2:
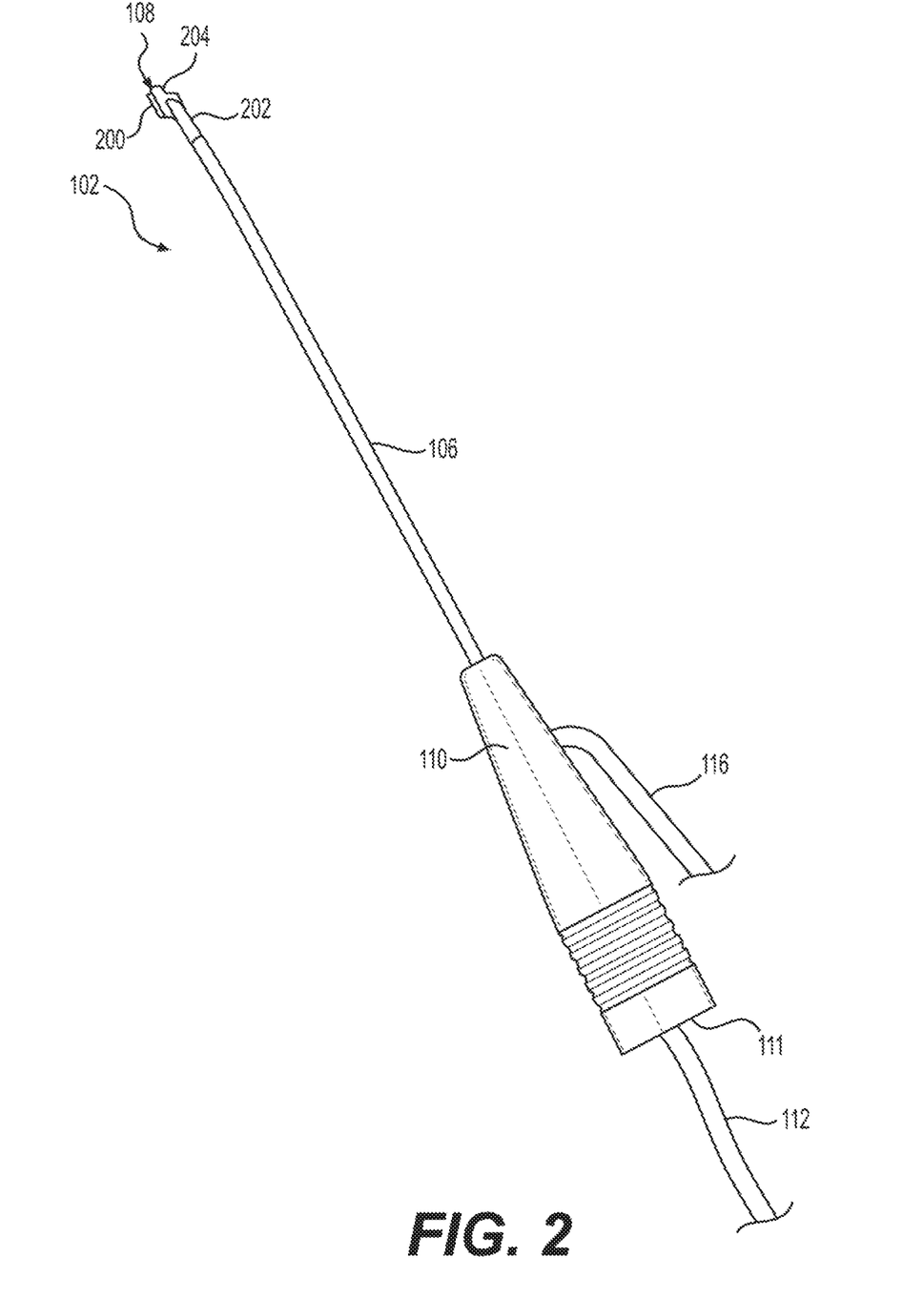
FIG. 2 shows an elevation view of an electrosurgical wand in accordance with at least some embodiments.

FIG. 2 shows a side elevation view of wand 102 in accordance with example systems. The wand 102 comprises elongate shaft 106 which may be flexible or rigid, and a handle 110 coupled to the proximal end 111 of the elongate shaft 106. At the distal end 108 resides an active electrode 200, a return electrode 202, and an electrode support member 204. The relationship of the various elements at the distal end 108 of the wand 102 will be discussed in greater below. Active electrode 200 may be coupled to an active or passive control network within controller 104 (FIG. 1) by means of one or more insulated electrical connectors (not shown) in the multi-conductor cable 112. The active electrode 200 is electrically isolated from a common or return electrode 202 which is disposed on the elongate shaft 106. Proximally from the distal tip, the return electrode 202 is concentric with the elongate shaft 106 of the wand 102. The support member 204 is positioned distal to the return electrode 202 and may be composed of an electrically insulating material such as epoxy, plastic, ceramic, silicone, glass or the like. Support member 204 extends from the distal end 108 of elongate shaft 106 (usually about 1 to 20 mm) and provides support for active electrode 200. Before describing the example wand in greater detail, the specification turns a brief discussion of the related-art devices.

Related-art electrosurgical devices, including plasma mediated systems, are used during shoulder arthroscopic surgery mostly to remove soft tissue in the sub-acromial space during a procedure called "sub-acromial decompression" (SAD). Most devices on the market use a geometry with the active electrode generally residing in a plane parallel to and displaced away from the shaft axis (sometimes referred to as 90 degrees perpendicular to the shaft axis, compared to an electrode that resides in a plane perpendicular to the shaft axis). The related-art electrodes and device tips are usually rounded and relatively flat to be atraumatic. However, devices with rounded tips do not provide very good access to any other tissues besides the bursa that needs to be removed during these procedures.

For other shoulder arthroscopy procedures, instruments with tip designs differing from those described in the immediately preceding paragraph are often used to allow better access to the target tissue. These other shoulder arthroscopy procedures may include tissue dissection of muscle planes, separation of the labrum for glenoid surface, sculpting of the labrum chondroplasty of the humeral head of glenoid surface or dissection to perform a Latarjet shoulder stabilization procedure. Using a different instrument for these procedures may add to the cost of the overall procedure. Moreover, when using a different instrument some pathology may not be treated, such as labrum or cartilage defects, where they could be treated with an appropriate Coblation® device.

Figure 3:
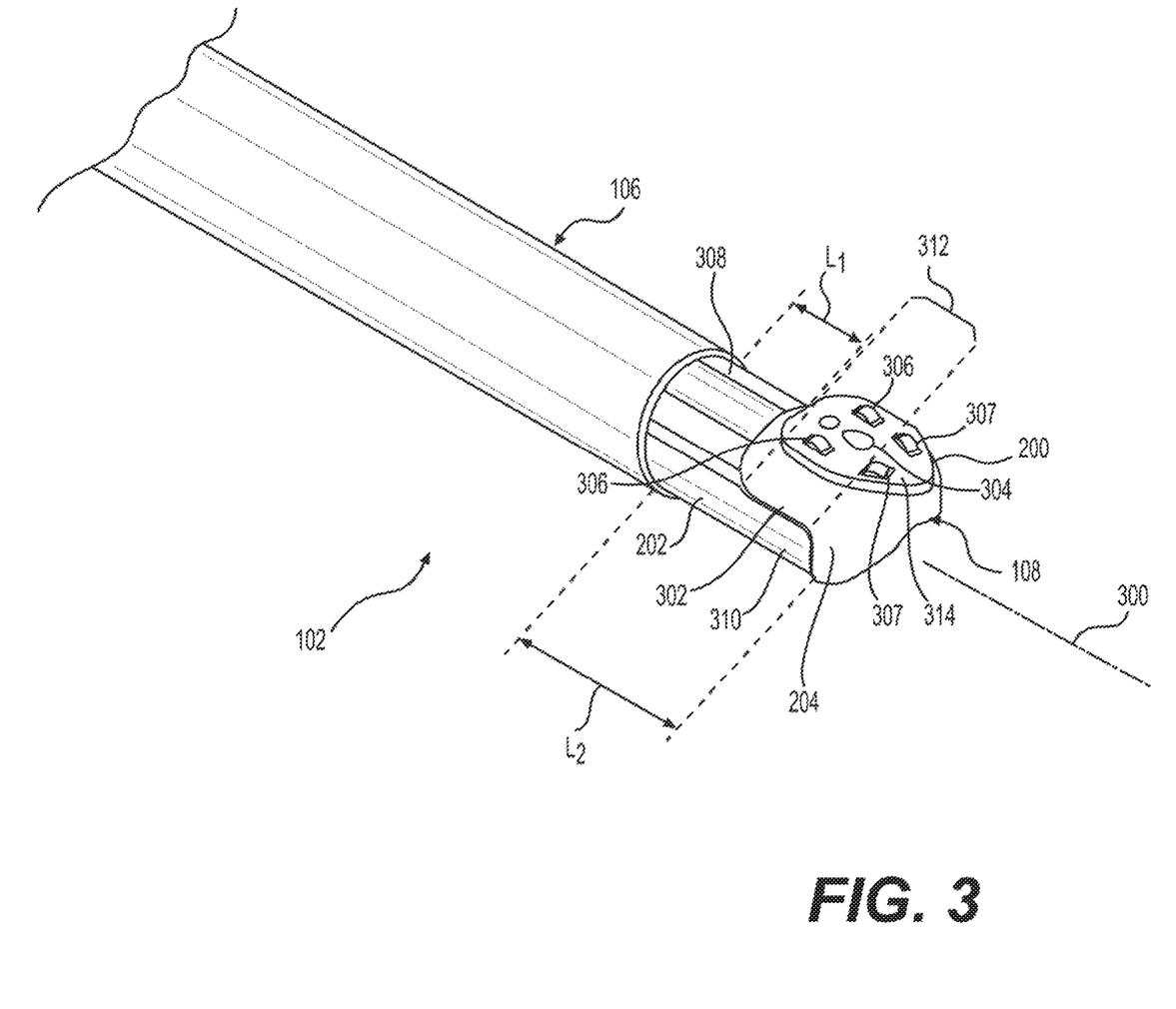
FIG. 3 shows a perspective view of a distal end of an electrosurgical wand in accordance with at least some embodiments.

FIG. 3 shows a perspective view of the distal end 108 of the wand 102 in accordance with example embodiments. In particular, visible in FIG. 3 is the elongate shaft 106 that extends along and defines a longitudinal central axis 300. Disposed at the distal end 108 is the return electrode 202. In the example system, the return electrode 202 also has a central axis that is coaxial with the longitudinal central axis 300. In more detail, the return electrode 202 abuts the elongate shaft 106 and extends along and annularly about the longitudinal central axis 300.

An electrode support device or support member 204 is coupled to the return electrode 202 at least partially distally thereof, and as the name implies the support member 204 supports the active electrode 200. In the example system, the active electrode 200 defines and resides within a plane, and in the embodiment shown the plane defined by the active electrode 200 is parallel to, spaced from, and extending along the longitudinal central axis 300. Stated otherwise, the example active electrode 200 faces outwardly at 90 degrees from the longitudinal central axis 300. The plane and active electrode 200 additionally extends laterally from the longitudinal central axis 300. In the example device shown, the longitudinal central axis 300 does not intersect the plane defined by the active electrode 200. However, in other example cases the support member 204 may orient the active electrode 200 at various angles. For example, if the active electrode 200 is sloped toward the distal end 108 of the wand 102, the longitudinal central axis 300 may intersect the plane distally of the wand 102. As another example, if the active electrode 200 is sloped toward the proximal end 111 (FIG. 2) of the wand 102, the longitudinal central axis 300 may intersect the plane proximally of the distal end 108 of the wand 102. Regardless, in example embodiments the longitudinal central axis 300 does not intersect the plane of the active electrode 200 within the exterior periphery 400 (FIG. 4A) of the active electrode 200.

Still referring to FIG. 3, in the example wand 102 shown, the return electrode 202 has a top side 308 adjacent the active electrode 200 and a bottom side 310 disposed remotely from the active electrode 200 and opposite the top side 308. The top side 308 of the return electrode 202 has a first length $L_1$ measured axially from the elongate shaft 106 and the bottom side 310 has a second length $L_2$ measured axially from the elongate shaft 106 being greater than the first length $L_1$ to define a notch or cutout 302, and the support member 204 telescopes within the return electrode 202 and resides within the notch 302. Thus, the return electrode 202 is not only defined proximally from the active electrode 200, but a portion of the return electrode 200 and the active electrode 200 overlap when measured or considered along the longitudinal central axis 300. More specifically, the notch 302 enables the bottom side 310 of the return electrode 202 and the active electrode 200 to overlap along the longitudinal central axis 300 in an overlap region 312. Thus, at least a portion of the return electrode 202 is disposed proximally to the active electrode 200.

Active electrode 200 in the example system defines an opening or aperture 304 therethrough. The aperture 304 is disposed above an opening in the support member 204 that is in fluid communication with the aspiration channel through the elongate shaft 106. Thus, the aperture 304 defines a suction lumen through the active electrode 200.

Finally with respect to FIG. 3, the example active electrode 200 further defines a plurality of protrusions 306, 307 and as shown, four such protrusions 306, 307. The plurality of protrusions 306, 307 extend away from the outer face 314 of the active electrode 200. Stated otherwise, the plurality of protrusions 306, 307 extend away from the outer face 314 of the active electrode 200 in a direction away from the longitudinal central axis 300.

Figure 4A:
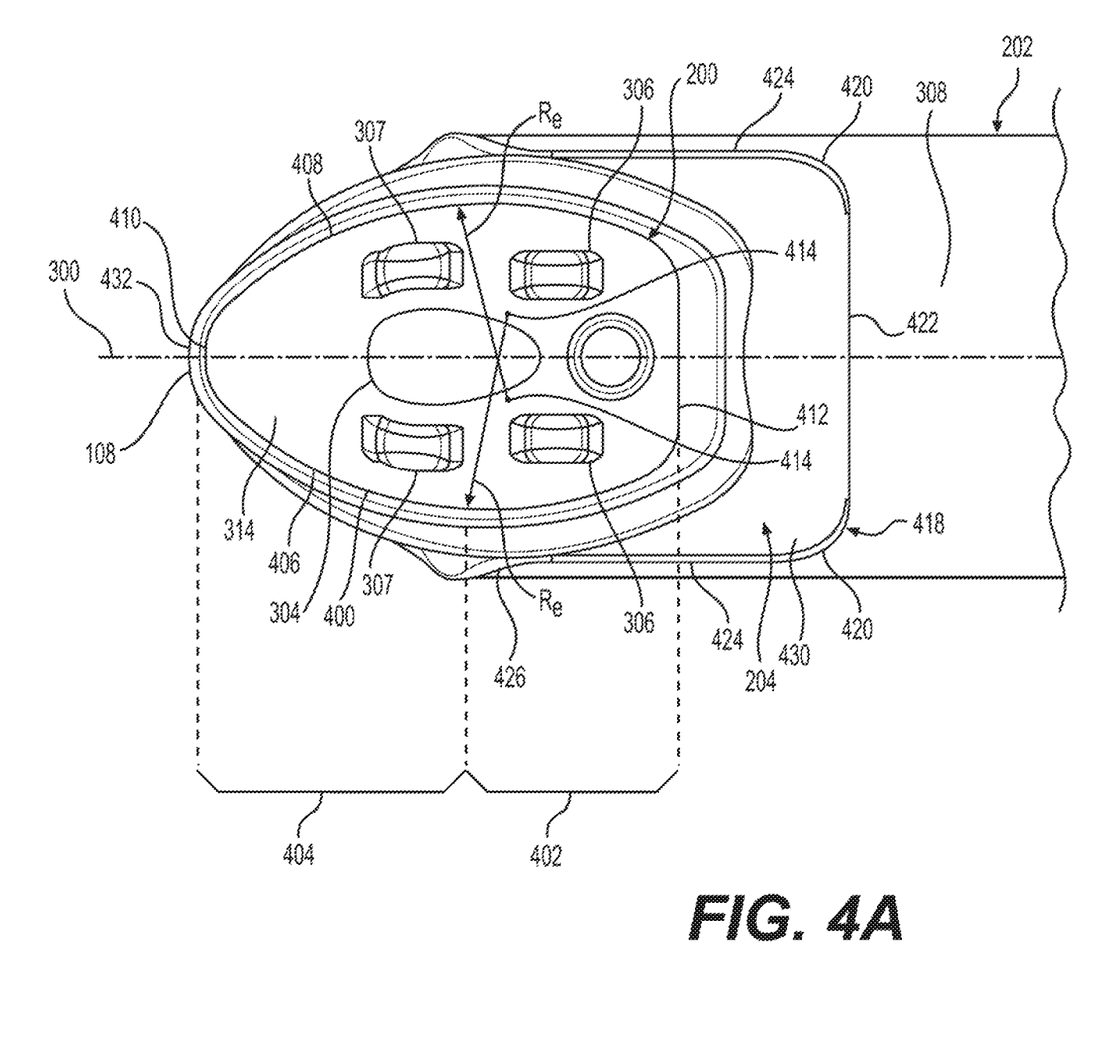
FIG. 4A shows an overhead view of an electrosurgical wand in accordance with at least some embodiments.

FIG. 4A shows an overhead view of the distal end 108 of the wand 102 of FIG. 3. In particular, visible in FIG. 4A is the active electrode 200, the support member 204, and the return electrode 202. The active electrode 200 in the example systems has the ovate or oblong shape when viewed perpendicular to the plane within which the active electrode 200 defines and resides (i.e., when viewed as in FIG. 4A). More particular, the example active electrode 200 defines an exterior periphery 400, a wider portion 402 and a narrower portion 404. The wider portion 402 is disposed proximal of the narrower portion 404, and the narrower portion 404 is disposed distally and narrows with increasing distal distance from the wider portion 402. The side edges 406 and 408 of the narrower portion 404 are shown to have a slightly convex shape, which may be helpful when the electrosurgical wand 102 is turned and the ablation performed along the side edges 406, 408. Furthermore, the side edges 406 and 408 converge with one another at an active electrode apex 410 in the narrower portion 404 and are connected at a truncated end 412 that is linear and extends laterally from the longitudinal central axis 300 in the wider portion 402. In more detail, the pair of side edges 406, 408 each has an edge radius of curvature $R_e$ having a center 414 on an opposite side of the longitudinal central axis 300 from the respective one of the pair of side edges 406, 408. In other cases, the side edges 406 and 408 may be straight and converge at the active electrode apex 410.

Also visible in FIG. 4A is the aperture 304. Thus, active electrode 200 and the aperture 304 form a screen electrode, and various ablation byproducts may be aspirated through the aperture 304. It should be understood that while one aperture 304 is shown, any number of apertures 304 may be used.

In addition, as best shown in FIG. 4A, the plurality of protrusions 306, 307 includes a pair of rear protrusions 306 spaced from and on opposite sides of the longitudinal central axis 300 in the wider portion 402 and a pair of front protrusions 307 spaced from and on opposite sides of the longitudinal central axis 300 and axially spaced from the rear protrusions 306 in the narrower portion 404. Also, the pair of front protrusions 307 each angles laterally inwardly toward the longitudinal central axis 300 as they extend axially away from the wider portion 402.

Figure 4B:
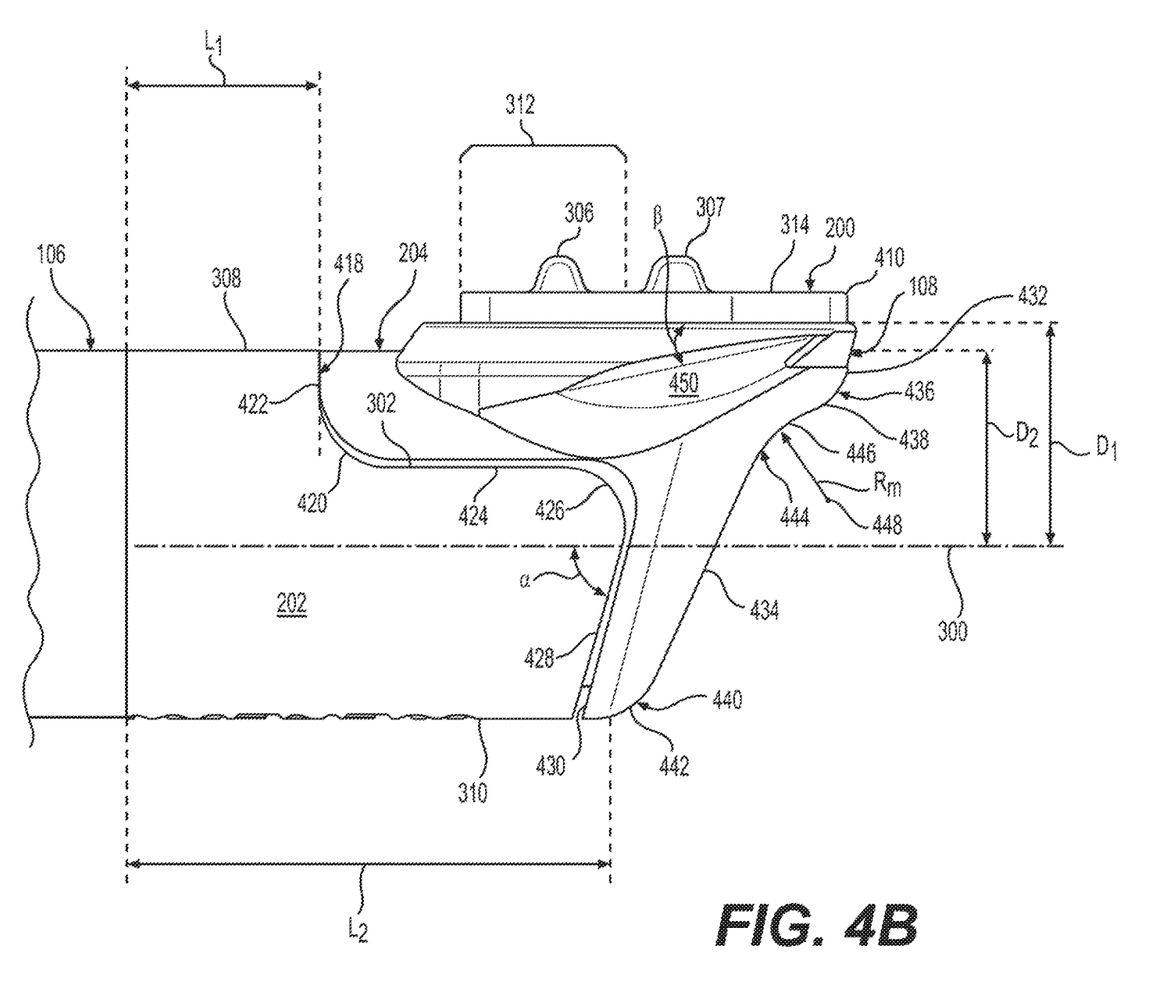
FIG. 4B shows of a side elevation view of the electrosurgical wand in accordance with at least some embodiments.

FIG. 4B shows a side-elevation view of the distal tip of the wand of FIGS. 3 and 4A. In particular, visible in FIG. 4B is the active electrode 200, the support member 204, the return electrode 202, and the elongate shaft 106. FIG. 4B illustrates several features, such as the notch 302 occupied by the support member 204, and which notch 302 enables overlap in the axial direction of the active electrode 200 and the return electrode 202. Moreover, two of the example protrusions 306, 307 (i.e., one each of the pair of rear protrusions 306 and the pair of front protrusions 307) are visible in the view of FIG. 4B, and again the plurality of protrusions 306, 307 extend from the outer face 314 of the active electrode 200.

The notch 302 defines a circuitous edge 418 extending arcuately across the top side 308 of the return electrode 202 between a pair of corners 420 to define an upper segment 422. The circuitous edge 418 also extends from the pair of corners 420 axially toward the distal end 108 to define a pair of horizontal segments 424 laterally opposite one another and each extending axially to end at respective shoulders 426. Additionally, the circuitous edge 418 extends from the shoulders 426 and extends arcuately around the bottom side 310 of the return electrode 202 to define a lower segment 428. As a result, the support member 204 includes a rear edge 430 extending along and corresponding with the circuitous edge 418 of the return electrode 202. Also, the lower segment 428 of the circuitous edge 418 is angled axially away from the distal end 108 as the circuitous edge 418 extends away from the longitudinal central axis 300 at a lower edge segment angle α relative to the longitudinal central axis 300. At least one of the shoulders 426 and the 420 corners is rounded or curved.

Moreover, FIG. 4B illustrates that the support member 204 transitions curvilinearly from the notch 302 of the return electrode 202 axially and tapers to a distal tip 432 adjacent the active electrode 200 to define a front surface 434 extending laterally across and axially from the return electrode 202 and tapering downwardly from the active electrode 200 to define a first portion 436 disposed adjacent the active electrode 200 and defining a first convex outer surface 438. The front surface 434 also extends toward the bottom side 310 of the return electrode 202 to define a second portion 440 disposed adjacent the bottom side 310 of the return electrode 202 and defining a second convex outer surface 442. Thus, the support member 204 holds the active electrode 200 a first distance $D_1$ from the longitudinal central axis 300 being greater than a second distance $D_2$ from the longitudinal central axis 300 to the top side 308 of the return electrode 202.

In some embodiments, the support member 204 has a mid-section 444 disposed between the first portion 436 and the second portion 440 of the front surface 434 that defines a concave outer surface 446 axially undercutting the active electrode 200 toward the proximal end 111 (FIG. 2). Specifically, the concave outer surface 446 has a member radius of curvature Rm having a center 448 on the same side of the longitudinal central axis 300 as the active electrode 200. However, it should be appreciated that various member radii of curvature $R_m$ and/or centers 448 may be utilized. The mid-section 444 creates "hook" that the surgeon may use to manipulate the placement of tissue during the surgical procedures. Nevertheless, the example support member 204 makes a relatively smooth transition to the distal tip 432 and makes a relatively smooth transition to the return electrode 202 to reduce the chances of inadvertently snagging or grabbing tissue.

Summarizing before continuing, the example active electrode 200 has an oblong shape, with the larger dimension or diameter more or less parallel to the longitudinal central axis of the elongate shaft 106 (FIG. 3). The oblong shape provides more or less flat side edges 406, 408 (slightly convex) for treating cartilage, a fine tip (i.e., active electrode apex 410 and distal tip 432) for soft tissue dissection, and a relatively low profile in both planes to be used as an instrument to manipulate different tissues as well. Although shown as a 90 degree tip, as discussed other angles of the active electrode 200 to the longitudinal central axis 300 are possible.

The support member 204 (e.g., ceramic) on which the active electrode rests also tapers toward the distal tip 432 in order to form a thinner assembly (e.g., FIG. 4A). FIG. 4B also shows that the ceramic, as it tapers has a mid-section 444 defining a concave outer surface 446 enabling a manipulation of tissue like a "hook."

Viewed from the "top" (FIG. 4A), the side edges 406 and 408 of the active electrode 200 are relatively close to the edge of the ceramic insulation that forms the support member 204, and the side edges 406 and 408 also have an almost straight or slight convex shape. The shape enables cartilage treatment when using the device on its side.

In some embodiments, the support member 204 can also have at least one shelf 450 extending axially along and spaced from the exterior periphery 400 of the active electrode 200. The shelf 450 is oriented or angled at a shelf angle β relative to the outer face 314 of the active electrode 200 and can be used as a visual marker for the location of the distal tip 432. According to an aspect, the shelf angle β can be between 30 and 60 degrees.

The example active electrode 200 is made of metal, in this case a metal injection mould made of an alloy mostly composed of tungsten. The active electrode 200 can have one or more apertures to form a suction lumen that removes both tissue debris and bubbles.

As discussed, the active electrode 200 may have features on the outer face 314 of the active electrode 200 such as the plurality of protrusions 306 (e.g., that may protrude 0.1-2.0 mm, an in other cases 0.3-1.02 mm) in order to provide better tactile feedback to the surgeon when treating tissue place on hard surface like bone. The features on the distal part of the active electrode 200 will also be designed such that when the active electrode apex 410 of the active electrode 200 is used at an angle and on its edge (e.g., to treat articular cartilage), the features remain at a distance from the cartilage surface so they do not affect the effect of the exterior periphery 400 (e.g., side edges 406, 408) of the active electrode 200 on tissue. In example cases the active electrode 200, and specifically the side edges 406 and 408, reside about 0.127 mm from the edge of the support member 204, while remaining portions of the active electrode 200 are set back a greater distance (e.g., about 0.356 mm at the proximal end of the active electrode 200). In example cases, the support member 204 is, at its widest, about 3.76 mm (measured perpendicular to the longitudinal central axis 300 and parallel to the plane of the active electrode 200). In example cases the width of the support member 204 just below the active electrode 200 (and again measured perpendicular to the longitudinal central axis 300 and parallel to the plane of the active electrode 200) may be about 3.30 mm, while the width of the active electrode 200 at the along the same measurement direction is about 3.05 mm. Finally, in example cases the thickness of the overall distal tip (measured from outer face 314 of the active electrode 200 to the bottom side 310 of the return electrode 202) is about 3.91 mm to about 4.34 mm. Other sizes are possible.

The versatility of the example wand design is further improved when used on an ablation platform which optimizes tissue effects for various type of tissue or anatomy. Further, the active electrode 200 could be split in two or more electrodes: a first electrode with the proximal part for gross tissue debulking, and the tip electrode (the distal "triangle") that used for fine dissection mode. Each electrode (i.e., separate parts of the active electrode 200) can be connected to a different output of the generator. Both electrodes or only the proximal electrode can be activated for gross debulking, while only the tip can be activated for more precision and lower power dissipation when needed for fine dissection or debridement of cartilage or meniscus.

The example devise may have a slightly smaller profile than related art 90° devices, with the same effect on soft tissue as related art 90° devices when used in shoulder sub-acromial decompression or knee notchplasty. However, the features described herein enable the device to be used for other procedures within shoulder and knee arthroscopy. The ability to perform the additional procedures provides a much more versatile device that saves time and or money for surgeons as more can be accomplished with a single device, thereby reducing the need to use or switch to a different type of instrument.

Figure 4C:
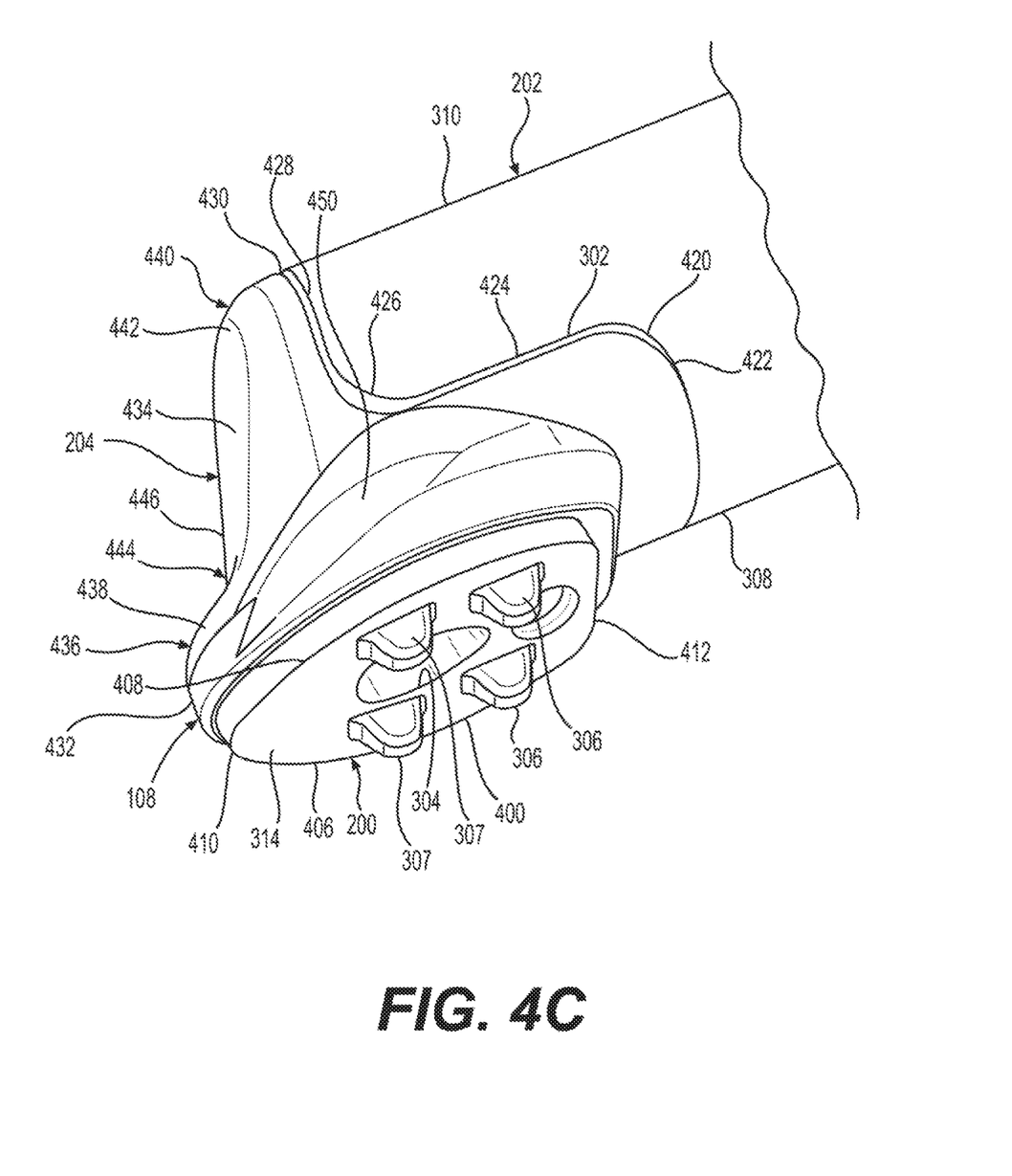
FIG. 4C shows another perspective view of the distal end of the electrosurgical wand in accordance with at least some embodiments.
Figure 4D:
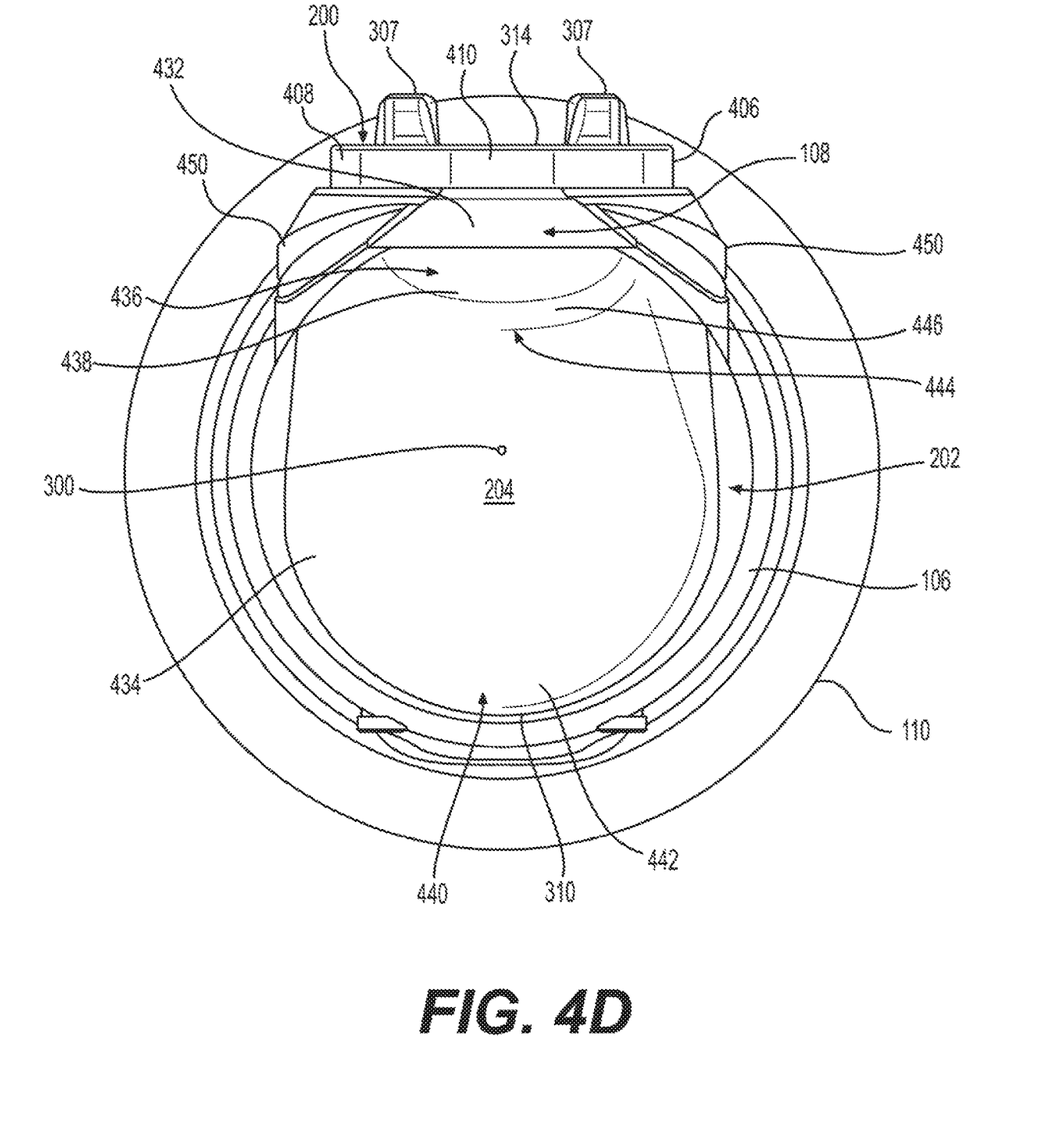
FIG. 4D shows an end view of the distal end of the electrosurgical wand in accordance with at least some embodiments.

FIGS. 4C and 4D show additional views of the distal end 108 of wand 102 in accordance with example embodiments.

Figure 5:
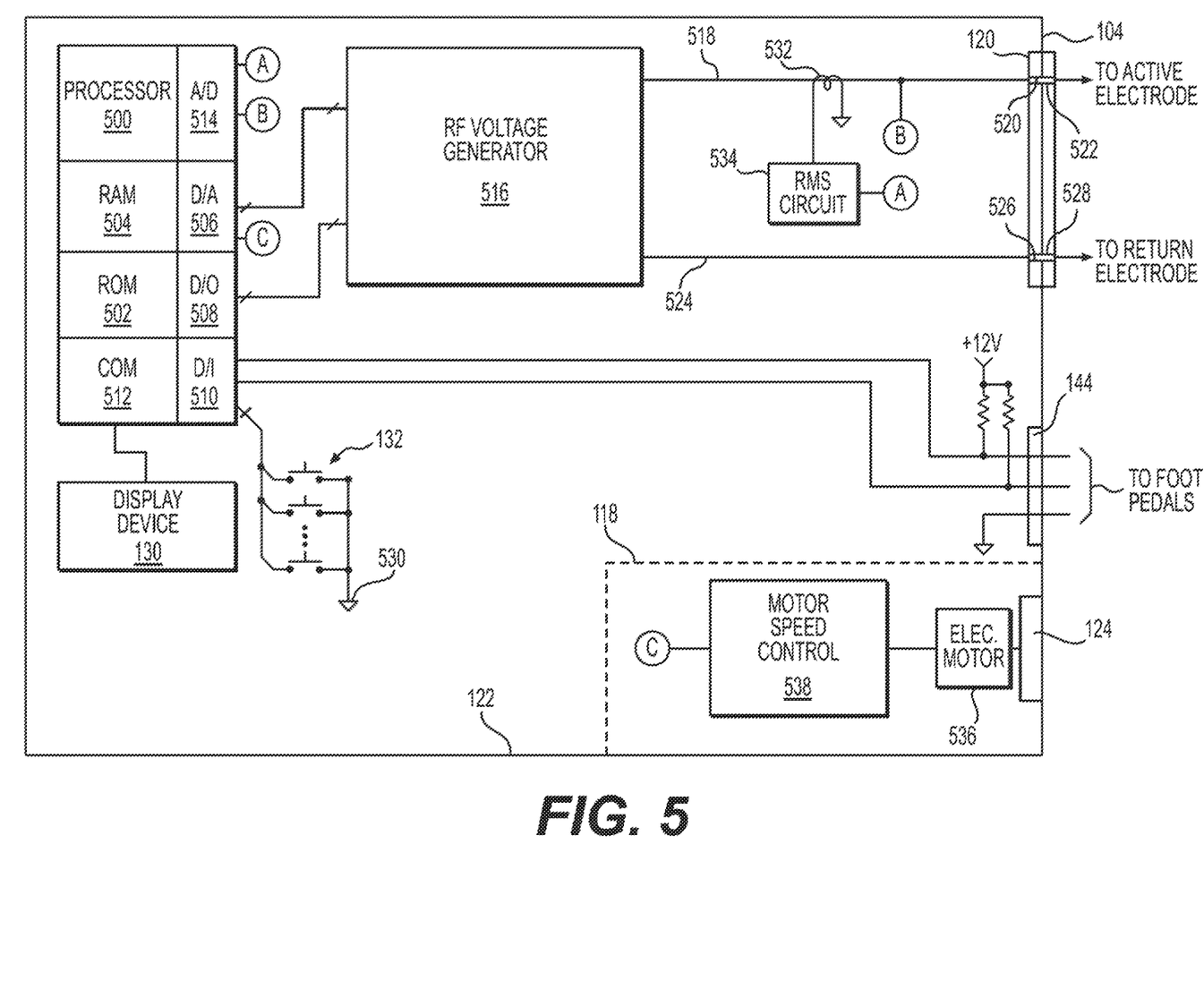
FIG. 5 shows an electrical block diagram of a controller in accordance with at least some embodiments.

FIG. 5 shows an electrical block diagram of controller 104 in accordance with at least some embodiments. In particular, the controller 104 comprises a processor 500. The processor 500 may be a microcontroller, and therefore the microcontroller may be integral with read-only memory (ROM) 502, random access memory (RAM) 504, flash or other non-volatile programmable memory, digital-to-analog converter (D/A) 506, analog-to-digital converter (A/D) 514, digital outputs (D/O) 508, and digital inputs (D/I) 510. The processor 500 may further provide one or more externally available peripheral busses (e.g., I$^2$C, USB). The processor 500 may further be integral with communication logic 512 (e.g., UARTs, Ethernet enabled ports) to enable the processor 500 to communicate with external devices, as well as internal devices, such as display device 130. Although in some embodiments the processor 500 may be implemented in the form of a microcontroller, in other embodiments the processor 500 may be implemented as a standalone central processing unit in combination with individual RAM, ROM, communication, A/D, D/A, DO, DI devices, and communication hardware for communication to peripheral components. In some example systems, the processor 500 and related functionality are implemented as a MK60 series microcontroller available from Freescale Semiconductor of Austin, Tex.; however, other microcontrollers may be equivalently used.

ROM 502 (or possibly a flash memory) stores instructions executable by the processor 500. In particular, the ROM 502 may comprise a software program that, when executed, causes the processor to sum, over various time windows, energy delivery and when needed temporarily cease or "pulse" the energy provided to ensure the rate of energy delivery does not exceed predetermined thresholds (discussed more below). The RAM 504 may be the working memory for the processor 500, where data may be temporarily stored and from which instructions may be executed. Processor 500 couples to other devices within the controller 104 by way of the digital-to-analog converter 506 (e.g., in some embodiment the RF voltage generator 516), digital outputs 508 (e.g., in some embodiment the RF voltage generator 516), digital inputs 510 (e.g., interface devices such as push button switches 132 or foot pedal assembly 134 (FIG. 1)), and communication device 512 (e.g., display device 130).

Voltage generator 516 generates an alternating current (AC) voltage signal that is coupled to active electrode(s) (e.g., active electrode 200) of the example wand. In some embodiments, the voltage generator defines an active terminal 518 which couples to electrical pin 520 in the controller connector 120, electrical pin 522 in the wand connector 114, and ultimately to the active electrode(s). Likewise, the voltage generator defines a return terminal 524 which couples to electrical pin 526 in the controller connector 120, electrical pin 528 in the wand connector 114, and ultimately to the return electrode(s). Additional active terminals and/or return terminals may be used. The active terminal 518 is the terminal upon which the voltages and electrical currents are induced by the voltage generator 516, and the return terminal 524 provides a return path for electrical currents. It would be possible for the return terminal 524 to provide a common or ground being the same as the common or ground within the balance of the controller 104 (e.g., the common 530 used on push-buttons 132), but in other embodiments the voltage generator 516 may be electrically "floated" from the balance of the controller 104, and thus the return terminal 524, when measured with respect to the common or earth ground (e.g., common 530) may show a voltage; however, an electrically floated voltage generator 516 and thus the potential for voltage readings on the return terminals 524 relative to earth ground does not negate the return terminal status of the terminal 524 relative to the active terminal 518.

The AC voltage signal generated and applied between the active terminal 518 and return terminal 524 by the voltage generator 516 is RF energy that, in some embodiments, has a frequency of between about 5 kilo-Hertz (kHz) and 20 Mega-Hertz (MHz), in some cases being between about 30 kHz and 2.5 MHz, in other cases being between about 50 kHz and 500 kHz, often less than 350 kHz, and often between about 100 kHz and 200 kHz. In some applications, a frequency of about 100 kHz is useful because target tissue impedance is greater at 100 kHz.

The RMS (root mean square) voltage generated by the voltage generator 516 may be in the range from about 5 Volts (V) to 1800 V, in some cases in the range from about 10 V to 500 V, often between about 10 V to 400 V depending on the mode of ablation and active electrode size. The peak-to-peak voltage generated by the voltage generator 516 for ablation in some embodiments is a square waveform in the range of 10 V to 2000 V, in some cases in the range of 100 V to 1800 V, in other cases in the range of about 28 V to 1200 V, and often in the range of about 100 V to 740 V peak-to-peak.

The voltage and current generated by the voltage generator 516 may be delivered as a square wave voltage signal or sine wave voltage with a sufficiently high frequency (e.g., on the order of 5 kHz to 20 MHz) such that the voltage is effectively applied continuously as compared with, e.g., lasers claiming small depths of necrosis, which are pulsed about 10 Hz to 20 Hz). In addition, the duty cycle of a square wave voltage produced by the voltage generator 516 is on the order of about 50% for some embodiments (e.g., half the time as a positive voltage square signal, and half the time as a negative voltage square signal) as compared with pulsed lasers which may have a duty cycle of about 0.0001%. Although square waves are generated and provided in some embodiments, the AC voltage signal is modifiable to include such features as voltage spikes in the leading or trailing edges of each half-cycle, or the AC voltage signal is modifiable to take particular shapes (e.g., sinusoidal, triangular).

The voltage generator 516 delivers average power levels ranging from several milliwatts to hundreds of watts per electrode, depending on the mode of operation and state of the plasma proximate to the active electrode(s). The voltage generator 516 in combination with the processor 500 are configured to set a constant root mean square (RMS) voltage output from the voltage generator 516 based on the mode of operation selected by the surgeon (e.g., one or more ablation modes, coagulation mode). A description of various voltage generators 516 can be found in commonly assigned U.S. Pat. Nos. 6,142,992 and 6,235,020, the complete disclosure of both patents are incorporated herein by reference for all purposes. Reference is also made to commonly assigned U.S. Pat. No. 8,257,350, titled "METHOD AND SYSTEM OF AN ELECTROSURGICAL CONTROLLER WITH WAVE-SHAPING", the complete disclosure of which is incorporated herein by reference as if reproduced in full below.

In some embodiments, the voltage generator 516 may be controlled by a program executing on the processor 500 by way of digital-to-analog converter 506. For example, the processor 500 may control the output voltages by providing one or more variable voltages to the voltage generator 516, where the voltages provided by the digital-to-analog converter 506 are proportional to the voltages to be generated by the voltage generator 516. In other embodiments, the processor 500 may communicate with the voltage generator by way of one or more digital output signals from the digital output converter 508, or by way of packet-based communications using the communication device 512 (the communication-based embodiments not specifically shown so as not to unduly complicate FIG. 5).

Still referring to FIG. 5, in some embodiment the controller 104 further comprises a mechanism to sense the electrical current provided to the active electrode. In the illustrative case of FIG. 5, sensing current provided to the active electrode may be by way of a current sense transformer 532. In particular, current sense transformer 532 may have a conductor of the active terminal 518 threaded through the transformer such that the active terminal 518 becomes a single turn primary. Current flow in the single turn primary induces corresponding voltages and/or currents in the secondary. Thus, the illustrative current sense transformer 532 is coupled to the analog-to-digital converter 514. In some cases, the current sense transformer may couple to the analog-to-digital converter 514 through amplification circuits, protection circuits, and/or circuits to convert the sensed values to RMS. In particular, in the example system of FIG. 5 the current sense transformer couples to an RMS circuit 534. RMS circuit 534 is an integrated circuit device that takes the indication of current from the current sense transformer 532, calculates a RMS value over any suitable period of time (in some example systems, over a 10 milli-second rolling window), and provides the RMS current values to the processor 500 through the analog-to-digital converter 514 (shown by bubble A). Other communicative couplings between the RMS circuit 534 and the processor 500 are contemplated (e.g., serial communication over an I²C or USB pathway, Ethernet communication). The current sense transformer 532 is merely illustrative of any suitable mechanism to sense the current supplied to the active electrode, and other systems are possible. For example, a small resistor (e.g., 1 Ohm, 0.1 Ohm) may be placed in series with the active terminal 518, and the voltage drop induced across the resistor used as an indication of the electrical current. Given that the voltage generator 516 is electrically floated, the mechanism to sense current is not limited to the just the active terminal 518. Thus, in yet still further embodiments, the mechanism to sense current may be implemented with respect to the return terminal 524. For example, illustrative current sense transformer 532 may be implemented on a conductor associated with the return terminal 524.

Still referring to FIG. 5, controller 104 in accordance with example embodiments further comprises the peristaltic pump 118. The peristaltic pump 118 may reside at least partially within the enclosure 122. The peristaltic pump comprises the rotor 124 mechanically coupled to a shaft of the electric motor 536. In some cases, and as illustrated, the rotor of the electric motor may couple directly to the rotor 124, but in other cases various gears, pulleys, and/or belts may reside between the electric motor 536 and the rotor 124. The electric motor 536 may take any suitable form, such as an AC motor, a DC motor, and/or a stepper-motor. To control speed of the shaft of the electric motor 536, and thus to control speed of the rotor 124 (and the volume flow rate at the wand), the electric motor 536 may be coupled to a motor speed control circuit 538. In the illustrative case of an AC motor, the motor speed control circuit 538 may control the voltage and frequency applied to the electric motor 536. In the case of a DC motor, the motor speed control circuit 538 may control the DC voltage applied to the electric motor 536. In the case of a stepper-motor, the motor speed control circuit 538 may control the current flowing to the poles of the motor, but the stepper-motor may have a sufficient number of poles, or is controlled in such a way, that the rotor 124 moves smoothly. Stated otherwise, the rotor 124 moves smoothly due to the high number of steps per turn. The processor 500 couples to the motor speed control circuit 536, such as by way of the digital-to-analog converter 506 (as shown by bubble C).

While preferred embodiments of this disclosure have been shown and described, modifications thereof can be made by one skilled in the art without departing from the scope or teaching herein. The embodiments described herein are exemplary only and are not limiting. Because many varying and different embodiments may be made within the scope of the present inventive concept, including equivalent structures, materials, or methods hereafter thought of, and because many modifications may be made in the embodiments herein detailed in accordance with the descriptive requirements of the law, it is to be understood that the details herein are to be interpreted as illustrative and not in a limiting sense.

What is claimed is:

1. An electrosurgical wand, comprising:
a handle on a proximal end of the electrosurgical wand;
an elongate shaft coupled to the handle and extending distally from the handle along a longitudinal central axis;
an active electrode disposed at a distal end of the electrosurgical wand and having an outer face and defining an exterior periphery extending thereabout and residing within and defining a plane spaced from and extending along and laterally from the longitudinal central axis;
a return electrode abutting the elongate shaft and extending along and annularly about the longitudinal central axis and having a top side adjacent the active electrode and a bottom side disposed remotely from the active electrode and opposite the top side, at least a portion of the return electrode being disposed proximally to the active electrode;
the top side of the return electrode having a first length measured axially from the elongate shaft and the bottom side having a second length measured axially from the elongate shaft being greater than the first length to define a notch enabling the bottom side of the return electrode and the active electrode to overlap along the longitudinal central axis in an overlap region;
a support member being electrically insulative and disposed in the notch between the active electrode and the return electrode and extending axially from the return electrode, the support member coupled to and supporting the active electrode; and
the support member transitioning curvilinearly from the notch of the return electrode axially and tapering to a distal tip of the support member, the support member distal tip having a contoured distal facing surface that forms a hook for accessing and manipulating target tissues, the hook being electrically insulative and disposed entirely between the active electrode and the central longitudinal axis.

2. The electrosurgical wand as set forth in claim 1, wherein the hook includes both a concave outer surface portion and a convex outer surface portion extending therefrom, transitioning smoothly therebetween to reduce inadvertent snagging or grabbing.

3. The electrosurgical wand as set forth in claim 1, wherein the hook includes a distal facing concave surface having a radius of curvature center that is disposed between the longitudinal central axis and the active electrode.

4. The electro surgical wand as set forth in claim 1, wherein the notch defines a circuitous edge extending arcuately across the top side of the return electrode between a pair of corners to define an upper segment and from the pair of corners axially toward the distal end to define a pair of horizontal segments laterally opposite one another and each extending axially to end at respective shoulders and from the shoulders extending arcuately around the bottom side of the return electrode to define a lower segment and wherein the support member includes a rear edge extending along and corresponding with the circuitous edge of the return electrode.

5. The electrosurgical wand as set forth in claim 4, wherein the pair of corners and horizontal segments of the return electrode are disposed between the longitudinal axis and the active electrode.

6. The electrosurgical wand as set forth in claim 1, further comprising: an aspiration channel defined within the elongate shaft; and wherein the active electrode further comprises at least one aperture that defines a suction lumen, the at least one aperture is disposed over an opening into the aspiration channel.

7. The electrosurgical wand as set forth in claim 1, wherein the support member includes at least one shelf extending axially along and disposed below the exterior periphery of the active electrode and extending laterally outwardly from the support member.

8. The electrosurgical wand as set forth in claim 7, wherein the at least one shelf is angled at a shelf angle relative to the active electrode outer face.

9. The electrosurgical wand as set forth in claim 8, wherein the shelf angle is between 30 and 60 degrees.

10. The electrosurgical wand as set forth in claim 1, wherein the hook is spaced distally from the entire return electrode.

11. An electrosurgical wand comprising:
a handle on a proximal end of the electrosurgical wand;
an elongate shaft coupled to the handle and extending distally from the handle along a longitudinal central axis;
an active electrode disposed at a distal end of the electrosurgical wand and having an outer face and residing within and defining a plane spaced from and extending along and laterally from the longitudinal central axis;
a return electrode abutting the elongate shaft and extending along and annularly about the longitudinal central axis and having a top side adjacent the active electrode and a bottom side disposed remotely from the active electrode and opposite the top side, at least a portion of the return electrode being disposed proximally to the active electrode;
a support member being electrically insulative and disposed between the active electrode and the return electrode and extending axially from the return electrode and coupled to and supporting the active electrode;
the active electrode having an oblong shape viewed perpendicular to the plane within which the active electrode resides with a wider portion and a narrower portion narrowing with increasing distal distance from the wider portion and disposed distally with respect to the wider portion and defining an exterior periphery extending thereabout including a pair of side edges; and
the active electrode including a plurality of protrusions extending away from the outer face of the active electrode in a direction away from the longitudinal central axis;
wherein the support member has a curvilinear distal facing surface including both a concave surface portion and a convex surface portion extending therefrom, wherein both the concave and convex surface portion are electrically insulative and disposed between the longitudinal central axis and the active electrode.

12. The electrosurgical wand as set forth in claim 11, wherein the plurality of protrusions includes a pair of rear protrusions spaced from and on opposite sides of the longitudinal central axis in the wider portion and a pair of front protrusions spaced from and on opposite sides of the longitudinal central axis and axially spaced from the rear protrusions in the narrower portion.

13. The electrosurgical wand as set forth in claim 12, wherein the pair of front protrusions each angles laterally inwardly toward the longitudinal central axis as they extend axially away from the wider portion.

14. The electrosurgical wand as set forth in claim 12, wherein the pair of side edges each is slightly convex and converges with one another at an active electrode apex in the narrowing portion and connected at a truncated end being linear and extending laterally from the longitudinal central axis in the wider portion.

15. The electrosurgical wand as set forth in claim 11, wherein the pair of side edges each has an edge radius of curvature having a center on an opposite side of the longitudinal central axis from the respective one of the pair of side edges.

16. The electrosurgical wand as set forth in claim 11, wherein the longitudinal central axis does not intersect the plane within the periphery of the active electrode.

17. The electrosurgical wand as set forth in claim 11, wherein the return electrode is entirely proximally separated from both the concave and convex surface portions.

18. The electrosurgical wand as set forth in claim 11, further comprising: an aspiration channel defined within the elongate shaft; and wherein the active electrode further comprises at least one aperture that defines a suction lumen, the at least one aperture is disposed over an opening into the aspiration channel.

19. An electrosurgical wand, comprising:
a handle on a proximal end of the electrosurgical wand;
an elongate shaft coupled to the handle and extending distally from the handle along a longitudinal central axis;
an active electrode disposed at a distal end of the electrosurgical wand and having an outer face and defining an exterior periphery extending thereabout and residing within and defining a plane spaced away from the longitudinal axis, and also extending along and laterally from the longitudinal central axis;
a return electrode disposed annularly about the longitudinal central axis; and
an electrically insulative support member disposed between the active electrode and the return electrode and extending axially from the return electrode, the electrically insulative support member coupled to and supporting the active electrode; wherein the electrically insulative support member has a curvilinear distal facing surface including a concave surface portion and a convex surface portion defining a distal-most tip of the electrically insulative support member that is disposed between the longitudinal central axis and the active electrode, for access to and fine dissection of target tissues.

* * * * *